(12) United States Patent
Cassuto et al.

(10) Patent No.: US 12,300,378 B2
(45) Date of Patent: May 13, 2025

(54) AUTOMATED SPERMATOZOA CANDIDATE IDENTIFICATION

(71) Applicant: BAIBYS FERTILITY LTD, Ramat-Gan (IL)

(72) Inventors: Nino Guy Cassuto, Tunis (TN); Gal Golov, Ramat-Gan (IL)

(73) Assignee: BAIBYS FERTILITY LTD, Ramat-Gan (IL)

( * ) Notice: Subject to any disclaimer, the term of this patent is extended or adjusted under 35 U.S.C. 154(b) by 360 days.

(21) Appl. No.: 17/793,146

(22) PCT Filed: Jan. 14, 2021

(86) PCT No.: PCT/IL2021/050049
§ 371 (c)(1),
(2) Date: Jul. 15, 2022

(87) PCT Pub. No.: WO2021/144800
PCT Pub. Date: Jul. 22, 2021

(65) Prior Publication Data
US 2023/0061402 A1 Mar. 2, 2023

Related U.S. Application Data

(60) Provisional application No. 62/961,844, filed on Jan. 16, 2020.

(51) Int. Cl.
*G16H 30/40* (2018.01)
*G06T 7/00* (2017.01)

(52) U.S. Cl.
CPC ........... *G16H 30/40* (2018.01); *G06T 7/0014* (2013.01); *G06T 2207/10016* (2013.01);
(Continued)

(58) Field of Classification Search
CPC ......... G06T 7/0014; G06T 2207/10016; G06T 2207/10056; G06T 2207/20081;
(Continued)

(56) References Cited

U.S. PATENT DOCUMENTS 10,255,693 B2 * 4/2019 Smith ...................... G06T 7/97
10,552,663 B2 * 2/2020 Smith .................. G06V 20/698
(Continued)

FOREIGN PATENT DOCUMENTS

CN           110458821 A       11/2019
WO        2019211596 A1       11/2019
WO    WO-2020090947 A1 *     5/2020

OTHER PUBLICATIONS

Nurhadiyatna, Adi, et al. "Comparison and implementation of motion detection methods for sperm detection and tracking." 2014 International Symposium on Micro-NanoMechatronics and Human Science (MHS). IEEE (Year: 2014).*
(Continued)

*Primary Examiner* — Scott A Rogers
(74) *Attorney, Agent, or Firm* — The Roy Gross Law Firm, LLC; Roy D. Gross

(57) ABSTRACT

A method comprising: receiving image data associated with a plurality of semen samples; at a training stage, training a machine learning model on a training set comprising: (i) said image data, and (ii) labels associated with a qualitative assessment of each of one or more individual spermatozoa in said semen samples; and applying said trained machine learning model to target image data associated with a target semen sample, to identify one or more spermatozoa in said target sample as candidates for an ART procedure.

18 Claims, 4 Drawing Sheets

(52) U.S. Cl.
 CPC .............. *G06T 2207/10056* (2013.01); *G06T 2207/20081* (2013.01); *G06T 2207/30024* (2013.01)

(58) Field of Classification Search
 CPC .......... G06T 2207/30024; G06V 10/82; G06V 20/69; G06V 20/693; G06V 20/695; G06V 20/698; G06V 20/70; G16H 30/40
 See application file for complete search history.

(56) References Cited

U.S. PATENT DOCUMENTS

| | | | | |
|---|---|---|---|---|
| 11,696,747 | B2* | 7/2023 | Thomas | G01N 33/487 356/338 |
| 2019/0197294 | A1 | 6/2019 | Demirci et al. | |
| 2021/0374952 | A1* | 12/2021 | Shafiee | H04N 23/55 |

OTHER PUBLICATIONS

Riordon, Jason, Christopher McCallum, and David Sinton. "Deep learning for the classification of human sperm." Computers in biology and medicine 111: 103342 (Year: 2019).*

Tan, Weng Chun, Nor Ashidi Mat Isa, and Mahaneem Mohamed. "Automated human sperm tracking using mean shift-collision detection and modified covariance matrix method." Multimedia Tools and Applications 79.39: 28551-28585 (Year: 2020).*

Valiuškaitė, Viktorija, et al. "Deep learning based evaluation of spermatozoid motility for artificial insemination." Sensors 21.1: 72 (Year: 2020).*

You, Jae Bem, et al. "Machine learning for sperm selection." Nature Reviews Urology 18.7: 387-403 (Year: 2021).*

Ottl, Sandra, et al. "A Machine Learning Framework for Automatic Prediction of Human Semen Motility." arXiv preprint arXiv: 2109.08049 (Year: 2021).*

Mirsky, S.K., Barnea, I., Levi, M., Greenspan, H. and Shaked, N.T., 2017. Automated analysis of individual sperm cells using stain-free interferometric phase microscopy and machine learning. Cytometry Part A, 91(9), pp. 893-900. doi: 10.1002/cyto.a.23189. Epub Aug. 22, 2017. PMID: 28834185.

Hicks, S.A., Andersen, J.M., Witczak, O. et al. Machine Learning-Based Analysis of Sperm Videos and Participant Data for Male Fertility Prediction. Sci Rep 9, 16770 (2019). https://doi.org/10.1038/s41598-019-53217-y.

McCallum, C., Riordon, J., Wang, Y. et al. Deep learning-based selection of human sperm with high DNA integrity. Commun Biol 2, 250 (2019). https://doi.org/10.1038/s42003-019-0491-6.

Mirsky, S.K., Barnea, I., Levi, M., Greenspan, H. and Shaked, N.T. (2017), Automated analysis of individual sperm cells using stain-free interferometric phase microscopy and machine learning. Cytometry, 91: 893-900. https://doi.org/10.1002/cyto.a.23189.

Wang R, Pan W, Jin L, Li Y, Geng Y, Gao C, Chen G, Wang H, Ma D, Liao S. Artificial intelligence in reproductive medicine. Reproduction. Oct. 2019;158(4):R139-R154. doi: 10.1530/REP-18-0523. PMID: 30970326; PMCID: PMC6733338.

PCT International Search Report for International Application No. PCT/IL2021/050049, mailed May 10, 2021, 5pp.

PCT Written Opinion for International Application No. PCT/IL2021/050049, mailed May 10, 2021, 8pp.

PCT International Preliminary Report on Patentability for International Application No. PCT/IL2021/050049, issued Jul. 19, 2022, 9pp.

* cited by examiner

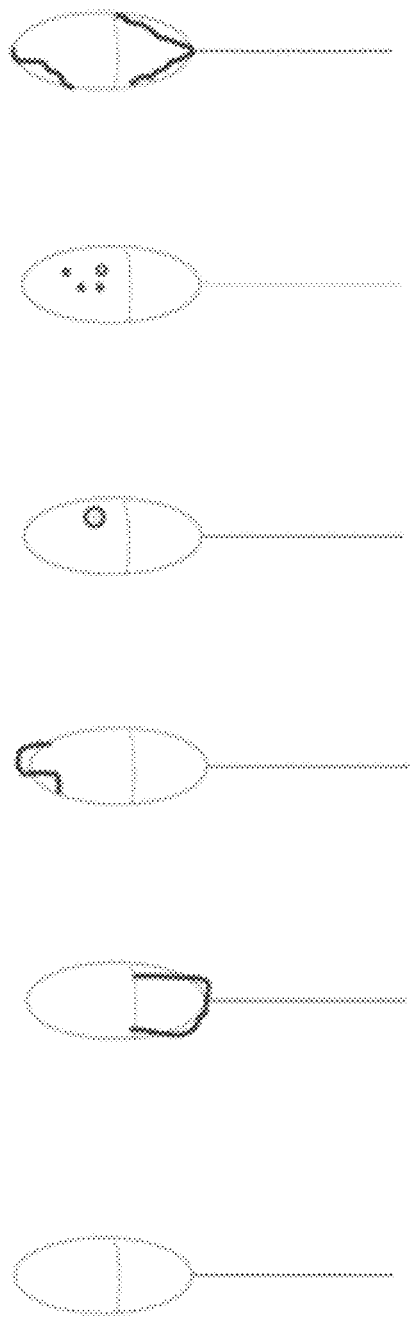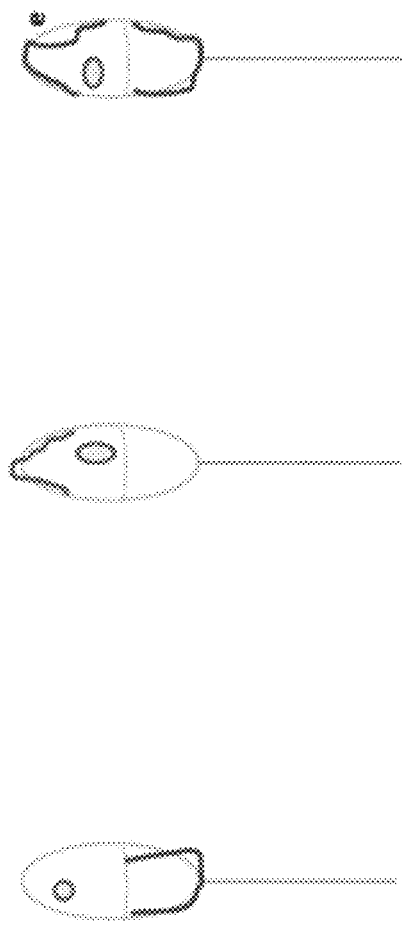

AUTOMATED SPERMATOZOA CANDIDATE IDENTIFICATION

CROSS REFERENCE TO RELATED APPLICATIONS

This application is a National Phase of PCT Patent Application No. PCT/IL2021/050049 having International filing date of Jan. 14, 2021, which claims the benefit of priority of U.S. Provisional Patent Application No. 62/961,844, filed Jan. 16, 2020, both entitled "AUTOMATED SPERMATOZOA CANDIDATE IDENTIFICATION", the contents of which are all incorporated herein by reference in their entirety.

FIELD OF THE INVENTION

The invention relates generally to the field of machine learning.

BACKGROUND

Infertility is a major global health concern with far-reaching social and demographic implications. Many of the present male reproductive technologies are mildly effective in treating male infertility. Technologies that can improve semen analysis and selection are pivotal for enhancing the effectiveness of treating male infertility.

Sperm morphology has been recognized to be a strong predictor of likelihood of successful outcomes, e.g., resulting in successful fertilization and/or successful pregnancies, in natural and/or assisted reproductive technology (ART). However, in many cases, the injected spermatozoa are randomly chosen, and their selection is based on rough morphological aspects and motility. Sperm quality is undoubtedly of the greatest importance in determining the quality of the developing embryo. For example, it has been reported that a paternal effect influences the blastocyst rate. Several points of negative impact, both genetic and epigenetic, have been identified in embryos after the sperm injection in the oocyte. Moreover, the selection and retrieval process for spermatozoon candidates exhibiting desirable characteristics remains a highly-specialized manual process, wherein accuracy and precision of output data may be affected by technician training, and subjective skill level, sample preparation, intensity of illumination, as well as instrument settings, specifications, and quality.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

There is provided, in an embodiment, a system comprising: at least one hardware processor; and a non-transitory computer-readable storage medium having stored thereon program instructions, the program instructions executable by the at least one hardware processor to: receive image data associated with a plurality of semen samples, at a training stage, train a machine learning model on a training set comprising: (i) said image data, and (ii) labels associated with a qualitative assessment of each of one or more individual spermatozoa in said semen samples, and apply said trained machine learning model to target image data associated with a target semen sample, to identify one or more spermatozoa in said target sample as candidates for an insemination procedure.

There is also provided, in an embodiment, a method comprising a method comprising: receiving image data associated with a plurality of semen samples; at a training stage, training a machine learning model on a training set comprising: (i) said image data, and (ii) labels associated with a qualitative assessment of each of one or more individual spermatozoa in said semen samples; and applying said trained machine learning model to target image data associated with a target semen sample, to identify one or more spermatozoa in said target sample as candidates for an insemination procedure.

There is further provided, in an embodiment, a computer program product comprising a non-transitory computer-readable storage medium having program instructions embodied therewith, the program instructions executable by at least one hardware processor to: receive image data associated with a plurality of semen samples; at a training stage, train a machine learning model on a training set comprising: (i) said image data, and (ii) labels associated with a qualitative assessment of each of one or more individual spermatozoa in said semen samples; and apply said trained machine learning model to target image data associated with a target semen sample, to identify one or more spermatozoa in said target sample as candidates for an insemination procedure.

In some embodiments, said qualitative assessment comprises estimation of a likelihood of success of an insemination procedure involving said individual spermatozoa.

In some embodiments, said qualitative assessment is based, at least in part, on one or more qualitative parameters selected from the group consisting of: detected motility, progressive motility, linear motility, morphology, base morphology, head morphology, and a presence and location of one or more vacuoles.

In some embodiments, the instructions are further executable to perform, and said method further comprises performing, an image processing stage, wherein said image processing comprises at least one of: image data cleaning, image data normalization, detection of individual spermatozoa in said image data, identification of individual spermatozoa in said image data, and tracking of individual spermatozoa in said image data.

In some embodiments, said tracking comprises identifying coordinates for at least one of said one or more spermatozoa in said target sample.

In some embodiments, said tracking further comprises operating a retrieval device to retrieve at least one of said one or more spermatozoa in said target sample, wherein said retrieval is based on said identified coordinates.

In some embodiments, the instructions are further executable to perform, and said method further comprises performing, a feature selection stage, wherein said feature selection comprises selection of one or more subsets of data points within the image data.

In some embodiments, said image data comprises, with respect to each of said semen samples, at least one of: a single image, a series of images, a video segment, a streamed video segment, and a real-time video segment.

In some embodiments, said identification comprises a confidence score assigned to said one or more spermatozoa in said target sample.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

FIGS. 4A, 4B, 4C, 4D, 4E, 4F, 4G, 4H, and 4I are schematic illustrations of exemplary features of spermatozoa identification, in accordance with some embodiments of the present invention.

DETAILED DESCRIPTION

Figure 1:
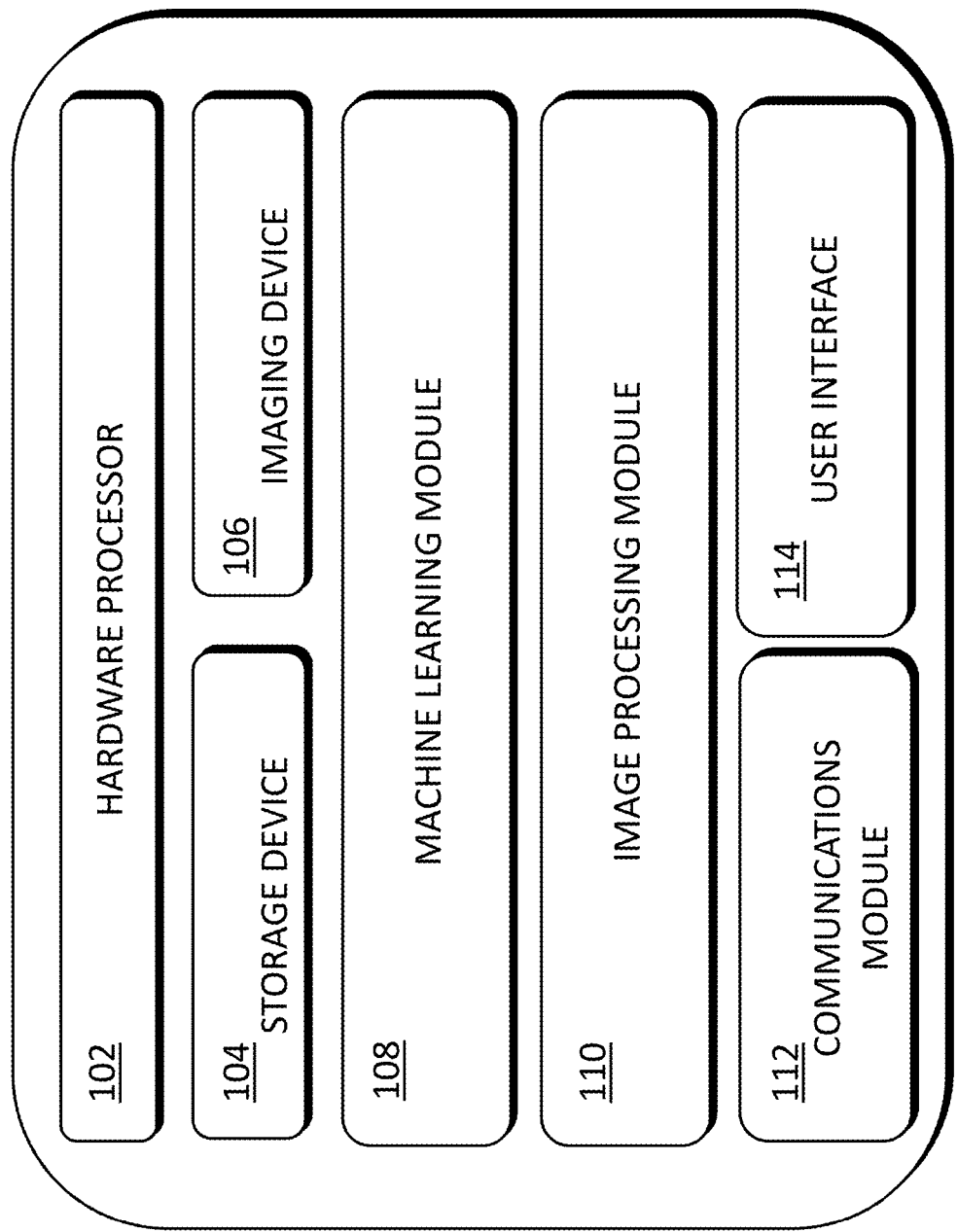
FIG. 1 is a block diagram of an exemplary system, according to an embodiment of the present invention.

The following embodiments and aspects thereof are described and illustrated in conjunction with systems, tools and methods which are meant to be exemplary and illustrative, not limiting in scope.

Disclosed herein are a method, system, and computer program product for automated detection of spermatozoon candidates in a semen sample, based on a qualitative assessment of a likelihood of successful outcomes in artificial insemination and/or with respect to assisted reproductive technology. In some embodiments, the present disclosure is thus particularly useful in the context of fertilization procedures such as, for example, assisted reproductive technology (ART), in-vitro fertilization (IVF), intra uterine insemination (IUI), and intra cytoplasmic sperm injection (ICSI), and in some embodiments, in assessing the spermatozoa quality for such procedures. In some embodiments, the present disclosure further provides for assessment of sperm quality in the exploration of male infertility.

In some embodiments, the present disclosure provides for determining whether one or more spermatozoa depicted in images of a semen sample are potential candidates for fertilization procedures, based on, e.g., a determination with respect to a fertility status and/or a likelihood of successful outcomes in one or more fertilization procedure using the specific spermatozoa.

For example, in order to determine which of the spermatozoa in a semen sample are candidates for fertilization procedures, image data reflecting, e.g., a single image, a series of images, and/or a video segment of a semen sample may be obtained.

In some embodiments, the image data may be produced by an imaging device, e.g., a video camera, directed at a semen sample placed in, e.g., a petri dish. In some embodiments, a monochromatic camera may be coupled to a microscope in order to obtain the images. In some embodiments, the obtained image data reflects high magnification, e.g., over 1000×. In some embodiments, the image data reflects magnification of between 1000×-6000×, e.g., at least 4000×. In some embodiments, the camera is a High-Resolution video Camera.

In some embodiments, the magnification reflects high magnification. In some embodiments, the magnification reflects differential interference contrast (DIC) microscopy. In some embodiments, high-power magnification is provided by an inverted light microscope with a magnification of, e.g., 1500× and/or with a zoom of at least 6100×. In some embodiments, the formula for the calculation of the final magnification is as follows: Magnification of the objective under the immersion oil (e.g., 100×), multiplied by the ocular (e.g., 10×), video adaptor (e.g., 1×), and monitor diagonal, and divided by a charge-coupled device with a magnification selector on the microscope (e.g., 1.6×).

A potential advantage of such high magnification (over 1000×) as described herein is in that some characteristics of the spermatozoon are noticeable only in higher magnification.

In some embodiments, the image data is obtained using one or more of RGB imaging techniques, monochrome imaging, near infrared (NIR), sort-wave infrared (SWIR), infrared (IR), ultraviolet (UV), multi spectral, hyperspectral, and/or any other and/or similar imaging techniques.

In some embodiments, the image data may be taken using different imaging techniques, imaging equipment, from different distances and angles, using varying backgrounds and settings, and/or under different illumination and ambient conditions.

In some embodiments, the obtained images undergo image processing analyses comprising at least some of: preprocessing, data cleaning, data normalization, and/or similar and/or additional image preprocessing steps. In some embodiments, image preprocessing may comprise the steps of detection, identification, and/or tracking of individual spermatozoa in the images. Accordingly, in some embodiments, a data preprocessing stage may comprise at least some of data derivation, data cleaning, data normalization, and/or additional similar operations with respect to the image data.

In some embodiments, a further data processing stage provides for applying dimensionality reduction and/or feature extraction and/or feature selection stage with respect to the image data.

In some embodiments, a location of spermatozoon candidates is detected within image data. In some embodiments, a location of spermatozoon candidates may be tracked within the sample. In some embodiments, a location of the spermatozoon candidates is detected and/or tracked within the sample, such that individual spermatozoon candidates may be retrieved for use in insemination procedures, e.g., by a suitable device, e.g., a micromanipulated needle for aspirating said selected individual spermatozoa. In some embodiments, the location of spermatozoon candidates is detected in two-dimensions (2D) or three-dimensions (3D). For example, the location of the spermatozoon candidates in a sample may be detected on a plane and/or in the depth dimension.

According to an aspect of some embodiments of the present invention there is provided a machine learning model trained to identify spermatozoon candidates in image data associated with a semen sample. In some embodiments, the present disclosure provides methods of evaluating spermatozoon candidates in semen sample data by applying a trained machine learning model to the semen sample image data.

In some embodiments, at a training stage, a machine learning model of the present disclosure is trained on a training set comprising image data associated with a plurality of semen samples. In some embodiments, the training set image data is annotated and/or labelled with labels associated with a qualitative assessment of one or more individual spermatozoa included therein.

In some embodiments, the training stage allows the machine learning model to detect features within the semen sample data and autonomously learn associations between the features and fertility status. In some embodiments, the trained machine learning model may be trained to classify detected spermatozoa into, e.g., two or more classes based, e.g., on a fertility status and/or a likelihood of successful outcomes in an insemination procedure of the spermatozoa.

In some embodiments, a training set of the present disclosure may be constructed by obtaining image data of multiple semen samples. In some embodiments, the training set comprises (a) image data obtained from one or more semen samples; and (b) labels associated with two or more classes with respect to individual spermatozoa in the samples. In some embodiments, the training comprises annotating individual spermatozoa depicted in the image data.

In some embodiments, the training set image data may comprise raw image data and/or extracted and/or selected features of the obtained image data. Accordingly, in some embodiments, a machine learning model and/or classifier of the present disclosure can be trained using a training set comprising features extracted from a plurality of images, sequences of image frames, video stream segments, and/or real-time video, wherein the data is associated with individual detected spermatozoa in the semen samples.

In some embodiments, the annotations and/or label associated with the training set are based, at least in part, on qualitative parameters and/or a qualitative assessment associated with an estimated success rate of fertility of individual spermatozoa in fertilization procedures. In some embodiments, the individual spermatozoa labels are categorized into two or more classifications. In some embodiments, the spermatozoa are categorized as "candidates" and "non-candidates" for fertilization procedures.

In some embodiments, the qualitative parameters may include, but are not limited to motility (such as motility grade), morphology, sperm concentration, total sperm count, MOT (motile total), and DNA and/or chromatin damage. In some embodiments, abnormalities of specific spermatozoa samples are detected and/or evaluated, such as hypospermia, hyperspermia, oligozoospermia, asthenozoospermia, teratozoospermia, necrozoospermia, epididymis and testicular spermatozoa.

In some embodiments, the data is annotated with spermatozoa attributes such as, but not limited to, motility, progressive motility, linear motility, morphology (e.g., tail morphology and mid-piece morphology), base morphology, head morphology, and a presence and location of one or more vacuoles. In some embodiments, the training set may be annotated to indicate, e.g., whether or not individual spermatozoa are candidates for fertilization procedures. In some embodiments, the spermatozoa are annotated manually by a specialist, e.g., an andrologist.

In some embodiments, at an inference stage, a trained machine learning model of the present disclosure may be configured to receive image data associated with a target semen sample, wherein the image data may be acquired from a single image, a series of images, and/or in a video segment. In some embodiments, the video segment may be a streamed video segment and/or a real-time video segment. In some embodiments, the trained machine learning model may be applied to the target sample image data to provide for a classification of one or more individual spermatozoa in the sample, based on a fertility status and/or a likelihood of successful outcomes in an insemination procedure of the spermatozoa.

In some embodiments, the present disclosure may further provide for location coordinates with respect to one or more spermatozoa in a target sample that are classified by the trained machine learning model as potential candidates. In some embodiments, based on such location coordinates, the present disclosure further provides for providing operational instructions and/or operating a suitable device to physically retrieve one or more of the spermatozoa so classified, for model is configured to track the location of the spermatozoon candidates. In some embodiments, the model is configured to send the location to a machine, e.g., a micromanipulated needle for aspirating said selected individual spermatozoon candidates.

A potential advantage of the present disclosure is, therefore, in that it provides for an automated, accurate and repeatable method to identify spermatozoon candidates for fertilization procedures, locating and/or tracking the identified candidate spermatozoa within the sample, and extracting the identified spermatozoa, using widely available and inexpensive imaging techniques and computer analysis tools.

Reference is made to FIG. 1, which is a block diagram of an exemplary system 100 according to an embodiment of the present invention. System 100 as described herein is only an exemplary embodiment of the present invention, and in practice may have more or fewer components than shown, may combine two or more of the components, or a may have a different configuration or arrangement of the components. The various components of system 100 may be implemented in hardware, software or a combination of both hardware and software. In various embodiments, system 100 may comprise a dedicated hardware device, or may form an addition to/or extension of an existing device.

System 100 may store in storage device 104 software instructions or components configured to operate a hardware processor 102 comprising such as hardware processor (also "hardware processor," "CPU," or simply "processor"). In some embodiments, the software components may include an operating system, including various software components and/or drivers for controlling and managing general system tasks (e.g., memory management, storage device control, power management, etc.) and facilitating communication between various hardware and software components.

In some embodiments, system 100 may comprise a hardware processor 102, a communications module 112, a user interface 114, an imaging device 106, an image processing module 110, and a machine learning module 108.

In some embodiments, the imaging device 106 may comprise any one or more devices that capture a stream of images and represent them as data. Imaging device 106 may be optic-based, but may also include depth sensors, infrared imaging sensors, and the like. In some embodiments, imaging device 106 may be coupled to and/or integral with a microscope. In some embodiments, imaging device 106 may be configured to detect RGB (red-green-blue) spectral bands. In other embodiments, imaging device 106 may be configured to detect at least one of monochrome, ultraviolet (UV), near infrared (NIR), short-wave infrared (SWIR), multiple spectral bands, and or hyperspectral imaging. In some embodiments, the imaging device 106 is configured to collect data in 2D and/or 3D. In some embodiments, the imagining device 106 comprises two or more separate devices configured to collect image data in 2D and/or 3D. For example, in some embodiments, the imaging device 106 is configured to obtain one or more of image data and depth image data of a semen sample.

In some cases, the produced data representing a stream of images can be in a format of data operable by a computer device for diverse purposes such as displaying the data, storing the image data, editing the data, and the like. In some embodiments, the data may be used at the analysis process of the video sequence. In some embodiments, such data can be used to derive various information aspects, which can be utilized in a number of processes such as detecting region of interest, segmentation, feature calculation, and the like. In some embodiments, such information can refer to color channels, e.g., red, green and blue. In some embodiments, the obtained images can be magnified optically and/or digitally. In some embodiments, the produced data can be magnified at high magnification. In some embodiments, the magnification may be by at least 100×, 1000×, 2000×, 4000×, 5000×, 6000×, or 7000×.

In some embodiments, the user interface 114 comprises one or more of a control panel for controlling system 100, buttons, display monitor, and/or speaker for providing audio commands. In some embodiments, system 100 includes one or more user input control devices, such as a physical or virtual joystick, mouse, and/or click wheel. In other variations, system 100 comprises one or more of peripheral interfaces, RF circuitry, audio circuitry, a microphone, an input/output (I/O) subsystem, other input or control devices, optical or other sensors, and an external port. Each of the above identified modules and applications correspond to a set of instructions for performing one or more functions described above. These modules (i.e., sets of instructions) need not be implemented as separate software programs, procedures or modules, and thus various subsets of these modules may be combined or otherwise re-arranged in various embodiments.

In some embodiments, the communications module 112 may be configured for connecting system 100 to a network, such as the internet, a local area network, a wide area network and/or a wireless network. In some embodiments, the communications module 112 facilitates communications with other devices over one or more external ports, and also includes various software components for handling data received by system 100. In some embodiments, the communications module 112 may be configured to enable communication between the machine learning module 108 and computerized processes, and/or data bases which may be reachable over the network.

In some embodiments, the image processing module 110 may be configured to receive image data, such as, e.g., video stream data, and process the data to extract and/or calculate a plurality of values and/or features derived from the data. In some embodiments, image processing module 110 may be configured to perform at least some of object detection, image segmentation, and/or object tracking based on one or more image processing techniques. In some embodiments, the present disclosure may combine object detection, tracking, and machine learning classification for tracking objects in a video stream and classifying segments of the objects as to whether they depict individual spermatozoa.

In some embodiments, the image processing module 110 may also be configured to calculate a plurality of frequency- and/or time-dependent features from the video stream data. In some embodiments, the features may represent various metrics derived from the video stream data, such as time domain, frequency domain, and/or other or similar features.

In some embodiments, the video stream data, values, and/or features extracted and/or calculated by image processing module 110 may be used to construct a training set for the training process of a machine learning classifier of the present disclosure. In some embodiments, the image processing module 110 may be configured to label and/or permit the labeling of calculated features associated with an image and/or video stream. In some embodiments, the process of labeling the features may involve user intervention which can be processed by the user interface 114. In some embodiments, the image processing module 110 may be configured to communicate with the machine learning module 108 for constructing the training sets required to train a classifier.

In some embodiments, the machine learning module 108 may be configured to train a machine learning model and/or classifier to detect individual spermatozoa in an image and/or video sequence. In some embodiments, the machine learning module 108 may be configured to train a machine learning classifier to identify spermatozoon candidates in an image and/or video sequence. In some embodiments, the image and/or video sequence may be associated with features calculated from data produced by the image processing module 110. In some embodiments, the machine learning module 108 can be configured to apply a trained machine learning classifier to a set of calculated target features to determine whether the image and/or video stream associated with the calculated features depicts spermatozoon candidates for fertilization procedures.

Figure 2:
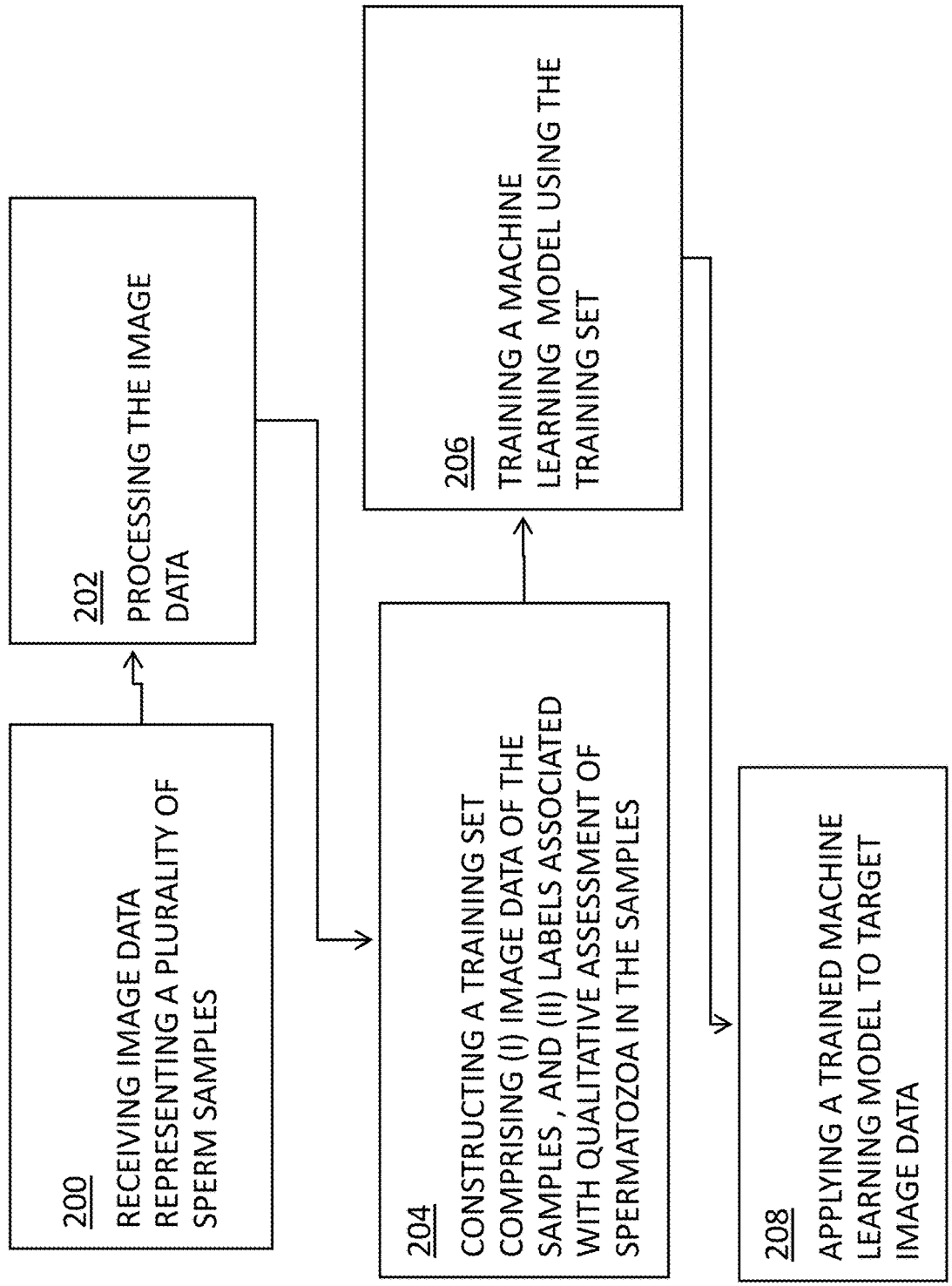
FIG. 2 is a flowchart of functional steps in a process for training a machine learning classifier to identify spermatozoon candidates in obtained data, in accordance with some embodiments of the present invention.

Reference is made to FIG. 2 which is a flowchart of functional steps in a process for training a machine learning classifier to identify spermatozoon candidates in image data, in accordance with some embodiments of the present invention.

In some embodiments, at step 200, image data of spermatozoa in a plurality of semen samples can be received by a system, such as system 100 in FIG. 1. In some embodiments, the image data can be obtained by an imaging device, such as imaging device 106. In some embodiments, the image data may be received as an input from an external source, e.g., the image data can be sent as an input from a storage device designed to manage a digital storage comprising images and/or video streams.

In some embodiments, the image data comprises an image, a series of images, a video segment, and/or a real-time video depicting one or more samples of semen. In some embodiments, the image data is magnified optically and/or digitally. In some embodiments, the image data reflects magnification of between 1000×-6000×, e.g., at least 4000×. In some embodiments, the image data comprises a real time video stream of the magnified moving spermatozoa. In some embodiments, the image data is stored onto a storage device, such as storage device 104.

For example, in some embodiments, the image data is received from a camera coupled to a microscope. In some embodiments, a trained embryologist adjusts the microscope in order to obtain an optimized focused image, for example, of an individual spermatozoon over various different sampling sites within a petri dish. In some embodiments, the image focus is optimized automatically.

In some embodiments, a thickener is added to the semen sample in order to increase the time available for adjustment of the microscope, thereby generating an optimized focused image. In some embodiments, the thickener comprises, e.g., polyvinylpyrrolidone (PVP). In some embodiments, the image data comprises a video segment and/or live video stream which includes the optimization of focus of the images. In some embodiments, the image data comprises a video segment and/or live video stream which comprises navigation between different sampling sites. In some embodiments, the image data comprises navigation between different sampling sites by following travel patterns of individual spermatozoa.

In some embodiments, the sampling sites are selected randomly. In some embodiments, the sampling sites are selected manually by a specialist. In some embodiments, the sampling sites are selected by user-input coordinates referring to locations within the sample and/or coordinates saved onto the storage device 104. In some embodiments, the sample sites are identified manually such that one or more subsets of data points within the image data depict individual spermatozoa.

In some embodiments, the semen samples are compressed, for example, within a cartridge. In some embodiments, the depth of the semen samples is compressed. A potential advantage of compressing the semen samples is in that the differences in focus due to different heights of the different spermatozoa is decreased.

At step 202 the image processing module 110 may apply one or more preprocessing and/or processing steps to the received and/or obtained image data. in some embodiments, image processing module 110 may divide the video stream into time windows, e.g., by defining a plurality of video sequences having, e.g., a specified duration, such as a five-second duration. In some embodiments, more than one sequence of frames may be chosen from one video stream.

In some embodiments, at step 202, the image processing module 110 may be configured to detect one or more regions-of-interest (ROI) in some or all of the frames in the video sequence, wherein the ROIs are potentially associated with individual spermatozoa. In some embodiments, at step 202, image processing module 110 may be configured to perform spermatozoa object detection. In some embodiments, detection is based, at least in part, on detection of spermatozoa head, base, nucleus, morphology, and/or motility. In some embodiments, ROI detection may be performed by using any appropriate image processing algorithms and/or methods.

At step 202, an image data processing step may be performed, e.g., by employing image processing module 110 in FIG. 1, to derive relevant data with respect to at least some of the segments in the ROI. In some embodiments, the processing stage may comprise data derivation, data cleaning, data normalization, and/or additional and/or similar operations with respect to the data.

In some embodiments, at step 202, one or more individual spermatozoa may be detected in the image data. In some embodiments, the ROI may be segmented, e.g., to areas considered as potentially associated with spermatozoa. In some embodiments, the ROI segments may be tracked throughout the image data, video segments, and/or live stream video.

Figure 3A:
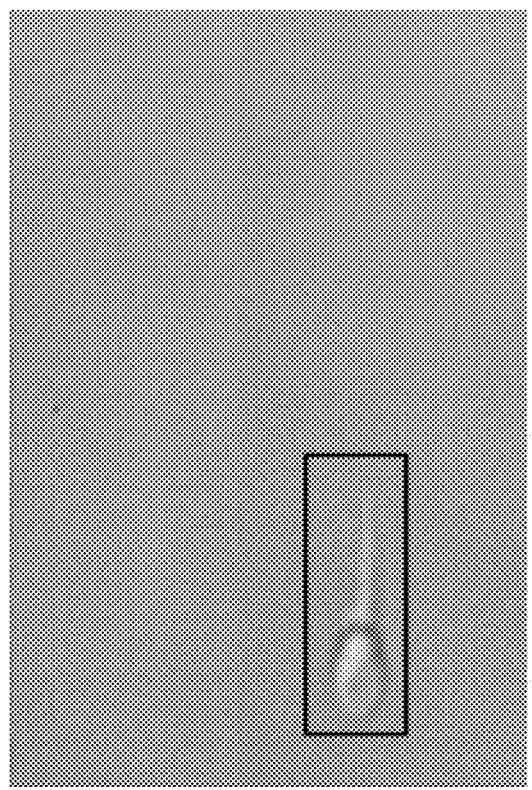
FIGS. 3A and 3B are exemplary data selection, in accordance with some embodiments of the present invention.
Figure 3B:
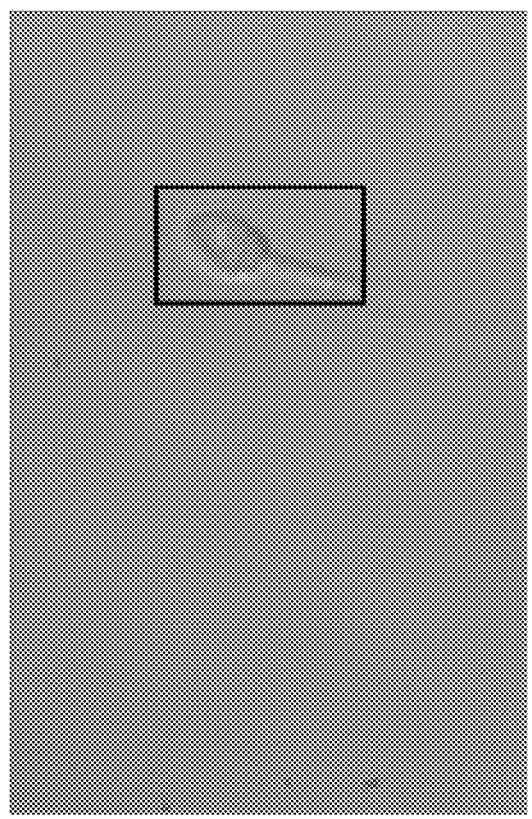

Reference is made to FIGS. 3A and 3B, which are exemplary data selection, in accordance with some embodiments of the present invention. In some embodiments, at step 202, the image data processing comprises data selection. In some embodiments, such as depicted by FIGS. 3A and 3B, the image data selection comprises selection of one or more subsets of data points within the image data, in which individual spermatozoa are depicted. In some embodiments, at step 202, the image data processing may comprise one or more of edge detection, corner detection, blob detection and/or extraction, ridge detection, scale-invariant feature transform, changing intensity, autocorrelation, thresholding, template matching, generalized Hough transform, deformable and parameterized shapes, and active contours. In some embodiments, at step 202, the image data processing may comprise shaped-based and/or flexible methods of optical character recognition. At step 202, in some embodiments, the image data so processed may be further be used for calculating a set of image data features.

In some embodiments, at step 202, a plurality of features may be extracted from the image data received at step 200. In some embodiments, the features calculated by the image processing module 110 can represent physical features of spermatozoa. For example, in some embodiments, the calculated features may include, in a non-limiting example, one or more of the morphology (e.g., head and/or base morphology), the cell size, the cell volume, the motility, and other attributes, such as, the presence of a vacuole in the nucleus of the cell. For example, in some embodiments, the shape of the head of the spermatozoa is labeled "H." For example, in some embodiments, the shape of the presence of a vacuole in the nucleus of the spermatozoa is labeled "V." For example, in some embodiments, the shape of the base of the head of the spermatozoa is labeled "B."

In some embodiments, at step 202, individual spermatozoa may be assigned a location within the image data, which may then be correlated with a universal coordinate system. The universal coordinate system allows the locations to be replicated on a different microscope system from a different manufacturer, a different design or having a different automated stage thereon. The universal coordinate system measures the location of individual spermatozoa from a fixed and/or moving physical feature on the semen sample. For example, in some embodiments, the universal coordinate system assigns each location x, y values for individual spermatozoa. For example, in some embodiments, the universal coordinate system assigns each location x, y, z values for individual spermatozoa. In some embodiments, the assigned location of individual spermatozoa is tracked throughout video segments and/or live video stream of the semen sample. In some embodiments, the assigned location of individual spermatozoa is tracked in 2D and/or 3D. In some embodiments, the assigned location of individual spermatozoa is tracked as a function of time and/or in real-time.

As may be appreciated by those skilled in the art, in real-life subject observation situations, several challenges emerge related to subject movement, lighting conditions, system latency, detection algorithms limitations, the quality of the obtained video, etc. For example, observed cells may not comprise an identical morphology for the duration of the observation. Accordingly, the predictive model of the present invention may be trained to adapt to a variety of situations and input variables.

In some embodiments, at step 204, system 100 may be configured for receiving image data for use in generating a training set for the prediction algorithm. The image data can comprise video sequences utilized in the training process, which can be captured from diverse imaging devices, with diverse types of resolution, imaging sensors, frame rates, etc.

In some embodiments, the training set may comprise a plurality of feature sets extracted from the received and/or stored image data. In some embodiments, the training set may be labelled to indicate, e.g., whether or not each of the individual spermatozoa is a candidate for fertilization procedures. In some embodiments, different fertilization procedures may include different training set labels.

In some embodiments, at step 204, a training set may be constructed, comprising (a) the feature sets extracted at step 202, and (b) labels indicating whether a corresponding image and/or video segment depicts a spermatozoa candidate for fertilization procedures. In some embodiments, the process of labeling the features may be manual and/or executed by a specialist, e.g., an andrologist.

In some embodiments, the labels are based, at least in part, on an assessment based on visual observation of each individual spermatozoa. In some embodiments, the visual assessment is used to determine if an individual spermatozoa is a candidate for fertilization procedures. In some embodiments, the assessment is of at least one of morphology-related attributes, motility-related attributes, and visual-related attributes. In some embodiments, the assessment is of one or more of sperm concentration, total sperm count, color, viscosity, and MOT (motile total). In some embodiments, the assessment is based on one or more of the motility, progressive motility, linear motility, morphology, base morphology, head morphology, and a presence and location of one or more vacuoles of each individual spermatozoon.

In some embodiments, at step 204, a specialist, e.g., an andrologist, may label one or more individual spermatozoa as "candidate" or "non-candidate." In some embodiments, the labels are based on individual parts of the spermatozoa. In some embodiments, the individual parts comprise one or more of the head of an individual spermatozoa, the base of an individual spermatozoa, and a tail of the individual spermatozoa. In some embodiments, the labels are based on visual attributes of the individual spermatozoa. In some embodiments, the labels reflect potential spermatozoa abnormalities.

Reference is made to FIGS. 4A-4I (collectively referred to herein as FIG. 4), which are schematic illustrations of exemplary features of spermatozoa identification, in accordance with some embodiments of the present invention. In some embodiments, the process of labeling the features may include labeling one or more of the shape of the head of an individual spermatozoa, the shape of the base of an individual spermatozoa, and the present of a vacuole in the nucleus of an individual spermatozoa, as depicted by FIG. 4.

For example, the individual spermatozoa depicted by FIG. 4A comprises an exemplary normal morphology. For example, the individual spermatozoa depicted by FIGS. 4B and 4G comprises normal morphology for the head of the individual spermatozoa and abnormal morphology for the base of the individual spermatozoa. For example, the individual spermatozoa depicted by FIGS. 4C and 4H comprise a normal morphology for the base of the individual spermatozoa and an abnormal morphology for the head of the individual spermatozoa. For example, the individual spermatozoa depicted by FIGS. 4F and 4I comprise an abnormal morphology of the head and the base of the individual spermatozoa. For example, the individual spermatozoa depicted by FIGS. 4D, 4E, 4G, 4H, and 4I comprise one or more vacuoles present within the head and/or base of the individual spermatozoa.

In some embodiments, potential spermatozoa abnormalities, such as, but not limited to, the abnormalities depicted by FIGS. 4, may indicate an individual spermatozoa that is not a candidate for fertilization procedures. In some embodiments, potential abnormalities may be given a quantitated confidence score, for example, between 1 and 100. In some embodiments, the individual spermatozoa can be labeled quantitatively such that the highest ranked spermatozoon are candidates for fertilization procedures. In some embodiments, the labels may include separate confidence scores for different potential abnormalities.

In some embodiments, at step 206, a machine learning model is trained using the training set constructed in step 204. In some embodiments, at step 206, a machine learning classifier may be trained to predict and/or classify a set of features extracted from a segment detected in image data, as depicting individual spermatozoa, e.g., based on a confidence score.

In some embodiments, at step 208, at an inference stage, a trained machine learning model of the present disclosure may be applied to image data from a target sample. In some embodiments, the target sample image data may be obtained, extracted, selected preprocessed, and/or processed based on at least some of the steps 200 and 202. In some embodiments, the machine learning model determines whether individual spermatozoa tracked in image data are candidates for fertilization procedures.

In some embodiments, the present disclosure provides for training a machine learning model to predict which individual spermatozoa are optimal candidates for fertilization procedures. In some embodiments, a training set for a machine learning model may comprise sets of spermatozoa features and/or potential abnormalities extracted from a plurality of semen samples, wherein each feature set and/or abnormality set is associated with an estimated success rate of fertility in fertilization procedures. In some embodiments, the feature sets and/or abnormalities may be obtained by employing the process detailed in steps 200-206 above.

In some embodiments, the machine learning model may be trained to predict a success level of the individual spermatozoa in a fertilization procedure. In some embodiments, the machine learning model may be further trained to compare the predicted success levels of individual spermatozoa.

In some embodiments, location of the optimal candidates detected at step 208 are tracked in real time. In some embodiments, the assigned location of the individual spermatozoa is stored in the storage device 104 of system 100.

In some embodiments, at step 202, the segments identified in the first frame of the sequence may also be tracked in subsequent frames throughout the sequence. In some embodiments, tracking segments throughout a video sequence may be performed by, e.g., checking a center of mass adjustment and/or polygon shape adjustment between consecutive frames in the sequence.

In some embodiments, the universal coordinate system measures the location of individual spermatozoa and outputs a real time update of the individual spermatozoa location within the semen sample.

In some embodiments, the real time spermatozoa position coordinates may be configured to provide operational instructions and/or to operate a suitable apparatus for retrieval of one or more individual spermatozoa. For example, in some embodiments, the device may be a micromanipulated needle for aspirating said selected individual spermatozoa. For example, in some embodiments, a capillary needle of the micromanipulator is configured to align with the spermatozoa location using the coordinate system. In some embodiments, the individual spermatozoa are pumped out from the semen sample, for example, to be put into a dedicated container. In some embodiments, the retrieval process may be accomplished by automated means.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object-oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a hardware processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

In some embodiments, separation, identification and/or imaging of spermatozoa further includes a microfluidic system. In some embodiments, the imaging or image analysis system and/or the computer program is connected to a microfluidic system. In some embodiments, the microfluidic system comprises a microfluidic chip.

In some embodiments, provided a system comprising: (a) a microfluidic channel; and (b) a photodetector, a photomultiplier tube (PMT), a radioactive detector, a camera or any combination thereof. In some embodiments, a photodetector, a photomultiplier tube (PMT), or a camera is connected to a computer comprising the method, system, and computer program product for automated detection of spermatozoon candidates in a semen sample. In some embodiments, a photodetector, a photomultiplier tube (PMT), or a camera is connected to a computer comprising the method, system, or computer program product for automated detection of spermatozoon candidates in a semen sample. In some embodiments, a photodetector, a photomultiplier tube (PMT), or a camera is connected to a system, or a computer program product for automated detection of spermatozoon candidates in a semen sample. In some embodiments, the method or system for automated detection of spermatozoon candidates in a semen sample comprises a photodetector, a photomultiplier tube (PMT), or a camera. In some embodiments, the method or system for automated detection of spermatozoon candidates in a semen sample is paired with high-speed imaging have resolved the full 3D swimming patterns of sperm in bulk fluid such as in a semen sample.

In some embodiments, a system and method as described herein further comprising a microfluidic system comprises: a microfluidic device, a fluid pump or electrodes, a camera, and an illumination source for illuminating a sperm cell within the camera field of view.

In some embodiments, the semen is mixed with a buffer in the separation channel within the microfluidic channel or device. In some embodiments, the semen is mixed with a buffer in the separation channel in order to reduce its viscosity. In some embodiments, the semen is mixed with a buffer in the separation channel in order to assume conditions of a Newtonian fluid.

In some embodiments, the microfluidic device is served for initial sorting of sperm cells based on their motility. In some embodiments, the microfluidic device is served for selecting motile sperm. techniques that do not require sperm motility have also been explored. In some embodiments, the microfluidic device is served to select sperm cells based on cell's size, shape, charge or any combination thereof. involves utilization of Raman spectroscopy in combination with microfluidic sperm sorting systems. In some embodiments, the microfluidic device comprises Raman spectroscopy for single cell analysis. In some embodiments, the microfluidic device transiently immobilizes motile sperm cells by means known in the art (such as but not limited to CaF2 coated wells). In some embodiments, each immobilized sperm cell is analyzed by Raman spectroscopy and/or a camera as described herein. In some embodiments, each immobilized sperm cell is illuminated by an illumination source as described herein.

The flowcharts and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the description and claims of the application, each of the words "comprise" "include" and "have", and forms thereof, are not necessarily limited to members in a list with which the words may be associated. In addition, where there are inconsistencies between this application and any document incorporated by reference, it is hereby intended that the present application controls.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

In the description and claims of the application, each of the words "comprise" "include" and "have", and forms thereof, are not necessarily limited to members in a list with which the words may be associated. In addition, where there are inconsistencies between this application and any document incorporated by reference, it is hereby intended that the present application controls.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system comprising:
   at least one hardware processor; and
   a non-transitory computer-readable storage medium having stored thereon program instructions, the program instructions executable by the at least one hardware processor to:
   receive series of images associated with a target semen sample,
   perform an image processing stage to detect one or more regions-of-interest (ROI) in the received series of images, said ROI associated with an individual spermatozoon in the target semen sample;
   apply a trained machine learning model to the detected one or more ROI, to calculate an estimated success rate of fertility of said individual spermatozoon in an insemination procedure; said trained machine learning model being trained on a training set comprising:
   (i) series of images associated with a plurality of semen samples, and
   (ii) labels associated with qualitative parameters associated with an estimated success rate of fertility of each of one or more individual spermatozoa in said plurality of semen samples in the insemination procedure, said qualitative parameters comprising morphology parameters and motility parameters; and
   identify said individual spermatozoon as a candidate for the insemination procedure, based on the estimated success rate.

2. The system of claim 1, wherein said motility parameters are selected from a group consisting of: detected motility, progressive motility, and linear motility, and wherein said morphology parameters are selected from a group consisting of: base morphology, head morphology, and a presence and location of one or more vacuoles.

3. The system of claim 1, wherein said comprises at least one of: image data cleaning, image data normalization, identification of said individual spermatozoa in said series of images associated with said target semen sample.

4. The system of claim 3, further comprising tracking of individual spermatozoon in said series of images associated with said target semen sample, wherein said tracking comprises identifying coordinates for said individual spermatozoon in said series of images associated with the target semen sample.

5. The system of claim 4, wherein said tracking further comprises operating a retrieval device to retrieve said individual spermatozoon from said target semen sample, and wherein said retrieval is based on said identified coordinates.

6. The system of claim 1, wherein said instructions are further executable to perform a feature selection stage, and wherein said feature selection comprises selection of one or more subsets of data points within the image data.

7. The system of claim 1, wherein said series of images comprise, with respect to each of said semen samples, at least one of: a video segment, a streamed video segment, and a real-time video segment.

8. The system of claim 1, wherein said identification comprises a confidence score assigned to said individual spermatozoon in said target semen sample.

9. A method comprising:
receiving series of images associated with a target sample semen;
performing an image processing stage to detect one or more regions-of-interest (ROI) in the received series of images, said ROI associated with an individual spermatozoon in the target semen sample;
applying a trained machine learning model to the detected one or more ROI, to calculate an estimated success rate of fertility of said individual spermatozoon in an insemination procedure, said trained machine learning model being trained on a training set comprising:
(i) series of images associated with a plurality of semen samples, and
(ii) labels associated with qualitative parameters associated with an estimated success rate of fertility of each of one or more individual spermatozoa in said plurality of semen samples in the insemination procedure, said qualitative parameters comprising morphology parameters and motility parameters; and
identifying said individual spermatozoon as a candidate for an insemination procedure, based on the estimated success rate.

10. The method of claim 9, wherein said motility parameters are selected from a group consisting of: detected motility, progressive motility, and linear motility, and wherein said morphology parameters are selected from a group consisting of: base morphology, head morphology, and a presence and location of one or more vacuoles.

11. The method of claim 9, wherein said image processing stage comprises at least one of: image data cleaning, image data normalization, identification of said individual spermatozoa in said series of images associated with said target semen sample.

12. The method of claim 11, further comprising tracking of individual spermatozoon in said series of images associated with said target semen sample, wherein said tracking comprises identifying coordinates for said individual spermatozoon from said target semen sample.

13. The method of claim 12, wherein said tracking further comprises operating a retrieval device to retrieve said individual spermatozoon from said target sample, and wherein said retrieval is based on said identified coordinates.

14. The method of claim 9, further comprising performing a feature selection stage, wherein said feature selection comprises selection of one or more subsets of data points within the image data.

15. The method of claim 9, wherein said series of images comprise, with respect to each of said semen samples, at least one of: a video segment, a streamed video segment, and a real-time video segment.

16. The method of claim 9, wherein said identifying comprises assigning a confidence score to said individual spermatozoon in said target semen sample.

17. A computer program product comprising a non-transitory computer-readable storage medium having program instructions embodied therewith, the program instructions executable by at least one hardware processor to:
receive series of images associated with a target semen sample;
perform an image processing stage to detect one or more regions-of-interest (ROI) in the received series of images, said ROI associated with an individual spermatozoon in the target semen sample;
apply a trained machine learning model to the detected one or more ROI, to calculate an estimated success rate of fertility of said individual spermatozoon in an insemination procedure, said trained machine learning model being trained on a training set comprising:
(i) series of images associated with a plurality of semen samples, and
(ii) labels associated with qualitative parameters associated with an estimated success rate of fertility of each of one or more individual spermatozoa in said plurality of semen samples in the insemination procedure, said qualitative parameters comprising morphology parameters and motility parameters; and
identify said individual spermatozoon as a candidates for an insemination procedure, based on the estimated success rate.

18. The computer program product of claim 17, wherein said motility parameters are selected from a group consisting of: detected motility, progressive motility, and linear motility, and wherein said morphology parameters are selected from a group consisting of: base morphology, head morphology, and a presence and location of one or more vacuoles, and
wherein said image processing stage comprises at least one of: image data cleaning, image data normalization, identification of individual spermatozoa in said series of images associated with said target semen sample, and tracking of individual spermatozoon in said series of images associated with said target semen sample.

* * * * *